(12) United States Patent
Spragins

(10) Patent No.: US 10,398,141 B1
(45) Date of Patent: Sep. 3, 2019

(54) BREAKABLE NONFLOWING GEL BAIT

(75) Inventor: Cisse W Spragins, Kansas City, MO (US)

(73) Assignee: ROCKWELL LABS LTD, North Kansas City, MO (US)

( * ) Notice: Subject to any disclaimer, the term of this patent is extended or adjusted under 35 U.S.C. 154(b) by 2051 days.

(21) Appl. No.: 12/009,353

(22) Filed: Jan. 17, 2008

(51) Int. Cl.
*A01N 27/00* (2006.01)
*A01N 25/00* (2006.01)
*A01M 1/20* (2006.01)
*A61K 8/73* (2006.01)

(52) U.S. Cl.
CPC ......... *A01N 25/006* (2013.01); *A01M 1/2055* (2013.01); *A61K 8/73* (2013.01)

(58) Field of Classification Search
CPC .................................................. A01M 1/2055
See application file for complete search history.

(56) References Cited

U.S. PATENT DOCUMENTS

| | | | |
|---|---|---|---|
| 4,664,857 A * | 5/1987 | Nambu | 264/28 |
| 5,021,237 A | 6/1991 | Bruey | |
| 5,126,139 A | 6/1992 | Geary | |
| 5,238,681 A | 8/1993 | Chang et al. | |
| 5,737,870 A | 4/1998 | Thind | |
| 5,850,707 A | 12/1998 | Fell et al. | |
| 5,871,765 A | 2/1999 | Johnson et al. | |
| 5,972,330 A | 10/1999 | Sugiura et al. | |
| 6,045,814 A | 4/2000 | Roulier et al. | |
| 6,352,693 B1 | 3/2002 | Kawada | |
| 6,645,949 B1 | 11/2003 | Nigg et al. | |
| 6,663,860 B1 * | 12/2003 | Tvedten | 424/94.63 |
| 7,179,455 B2 | 2/2007 | Marshall | |
| 2002/0076387 A1 * | 6/2002 | Birkel et al. | 424/70.1 |
| 2004/0057977 A1 * | 3/2004 | Gardner et al. | 424/410 |
| 2010/0028295 A1 * | 2/2010 | Taranta et al. | 424/84 |

OTHER PUBLICATIONS

Rockwell Labs Ltd, InTice Thiquid Ant Bait, catalog sheet, 2007, Rockwell Labs Ltd, North Kansas City, MO.
Senoret Chemical Company, Terro Liquid Ant Bait, web advertisement page from www.terro.com, 2006, Senoret Chemical Company, St. Louis, MO.
Rockwell Labs Ltd, InTice Sweet Ant Gel, catalog sheet, 2007, Rockwell Labs Ltd, North Kansas City, MO.
Rockwell Labs Ltd, InTice Roach Bait, catalog sheet, 2007, Rockwell Labs Ltd, North Kansas City, MO.
The Dial Corporation, Combat Quick Kill, web advertisement page from www.dialcorp.com, 2008, The Dial Corporation, Scottsdale, AZ.
Whitmire Micro-Gen Research Laboratories, Inc., Advance Termite Bait Cartridge (TBC), web advertisement page from www.wmmg.com, 2007, Whitmire Micro-Gen Research Laboratories, Inc., St. Louis, MO.
Whitmire Micro-Gen Research Laboratories, Inc., Avert Dry Flowable Cockroach Bait Formula 1, web advertisement page from www.wmmg.com, 2007, Whitmire Micro-Gen Research Laboratories, Inc., St. Louis, MO.
Rockwell Labs Ltd, InTice Granular Bait, catalog sheet, 2007, Rockwell Labs Ltd, North Kansas City, MO.
Bell Laboratories, Inc., Contrac, web advertisement page from www.belllabs.com, 2008, Bell Laboratories, Inc., Madison, WI.
Bell Laboratories, Inc., Liqua-Tox, web advertisement page from www.belllabs.com, 2008, Bell Laboratories, Inc., Madison, WI.

* cited by examiner

*Primary Examiner* — Kyle A Purdy

(57) ABSTRACT

A breakable nonflowing gel bait composition that includes water in a range of about 40% to about 99% by weight of the composition, a toxicant in a range of about 0.0001% to about 25% by weight of the composition, one or more attractants in a combined range from about 1% to about 49% by weight of the composition, a gelling agent in a range of about 0.001% to about 15% by weight of the composition, and wherein the breakable nonflowing gel bait composition is a breakable nonflowing gel.

21 Claims, 1 Drawing Sheet

BREAKABLE NONFLOWING GEL BAIT

FIELD OF THE INVENTION

The present invention generally relates to bait compositions for pests such as insects and other arthropods, and rodents, more particularly to such compositions that take the form of a gel, and specifically to such compositions that take the form of a breakable nonflowing gel packaged in a ready-to-use bait container.

BACKGROUND OF THE INVENTION

Pesticidal baits in various forms have been in use for many years. Current insect and other arthropod bait formulas take the form of liquid or syrup baits (for example InTice Thiquid Ant Bait, or Terro pre-filled stations); gels or pastes packaged in syringes or squeeze tubes (for example, InTice Sweet Ant Gel, InTice Roach Bait) or in aerosol or pressurized cans (for example U.S. Pat. Nos. 5,126,139 and 5,021,237); semi-solid wax or oil based baits deployed in ready-to-use stations (for example, Combat roach baits); spreadable pastes packaged in jars; pressed or loose powder baits (for example, Advance Termite Bait, Avert Dry Flowable Cockroach Bait); and granular baits (for example, InTice Granular Bait). Rodent baits take the form of dry pellets, meal, grain, seed, or wax blocks (for example, Contrac rodent baits); or liquids (for example, Liqua-Tox II). Dry granular type rodent baits are often packaged in ready-to-use "place packs" that are placed as such in the control environment. The rodent that encounters the place pack then chews through the package to obtain the bait inside. Prior to that time, the bait is contained and protected. Fat-based paste rodent baits packaged in jars or squeeze or syringe-type tubes are also sold outside the United States (none known in the United States at this time).

Liquid baits have the advantage of being highly attractive to insects due to the moisture content and the ease of consuming the product for the insect. For rodents, liquid baits can be very attractive in facilities with large amounts of alternative food but limited water supply, such as grain storage facilities. Liquid baits have the disadvantage of being spillable, potentially messy to use, and needing generally to be deployed in some sort of container. Indeed, there are numerous patents which address intricate pest station configurations that can be used to minimize spilling of liquid baits (for example, U.S. Pat. Nos. 6,467,216; 7,204,054 and 6,216,384). For ants and other small insects, liquid baits have the further disadvantages that the insect may drown in the bait, or in the case of sticky or syrupy baits, get stuck in the bait, and send out an alarm signal to other insects that might feed. Furthermore, insects can only feed safely around the edges of the liquid bait, which decreases the number of insects that can feed at one time. For successful control, it is best if numerous insects feed at once and the insects then take the bait back to the nest to share.

Squeezable gels and pastes packaged in syringes or other dispensing tubes have the advantage that they can be injected into cracks where pests often harbor. Often they are thick and sticky in texture which allows them to be placed in up and out of the way places. Depending on the specific formulation, they have various disadvantages, namely: they are difficult to remove after treatment, unless placed in a bait station; if they have low moisture content, they are less attractive to pests in certain situations, if they have a high moisture content but can still be squeezed easily out of a tube, they are frequently runny and messy, and don't stay where they are placed; if they are sticky so that they stick easily to the surfaces they are applied to, they are also sticky to insects, and more difficult for insects to ingest; those with relatively high moisture content frequently dry out rather quickly after application and then become less attractive to pests, or may harden to the point that pests cannot ingest them at all.

Semi-solid or solid, oil or wax-based baits deployed in ready-to-use stations are easy to use, but they don't have the moisture content that is highly attractive to pests in certain instances. Similarly, dry baits in powder, granular, pellet, meal, grain, seed, or wax block form, are convenient to use and well-suited to certain control situations, but do not have the moisture content that is highly attractive to pests in certain instances.

SUMMARY OF THE INVENTION

The present invention combines the advantages of the high-moisture content of liquid baits, with the "mess-free" ready-to-use convenience of a dry bait packaged in a bait station, bait cartridge or bait "place pack".

A feature of the present invention is the provision in a bait composition for insects and other arthropods or rodents, of the bait composition taking the form of a breakable, non-flowing gel.

Another feature of the present invention is the provision in a breakable nonflowing gel bait composition, of the breakable nonflowing gel having a melting point of at least 100° F.

Another feature of the present invention is the provision in the breakable nonflowing gel bait composition, of the breakable nonflowing gel having a first physical shape attained at manufacture, wherein the breakable nonflowing gel bait composition has a second physical shape when deployed in an end use environment, and wherein the first physical shape and the second physical shape are substantially the same.

Another feature of the present invention is the provision of the breakable nonflowing gel bait composition, of one and only one container for the breakable nonflowing gel bait composition throughout its lifetime as a product, wherein the container is the container employed at manufacture and receives the breakable nonflowing gel bait composition when the breakable nonflowing gel bait composition is in a heated and flowing form, wherein the container is the container in which the breakable nonflowing gel bait composition cools to the final breakable nonflowing gel form, and wherein the container is the container employed in an end use environment such that the container is the container confronted by the pest that is being targeted.

Another feature of the present invention is the provision in the breakable nonflowing gel bait composition, of the combination of water in a range of at least 40% by weight of the composition, a pesticidal toxicant in an effective concentration, and an appropriate gelling agent in a concentration sufficient to yield the breakable nonflowing gel with a melting point of at least 100° F.

Another feature of the present invention is the provision in the breakable nonflowing gel bait composition, of the combination of water in a range of about 40% to about 99% by weight of the composition, a toxicant in a range of about 0.0001% to about 25% by weight of the composition, a humectant in a range of about 0.1% to about 25% by weight of the composition, one or more attractants in a range from about 1% to about 49% by weight (combined) of the composition, one or more preservatives in a combined range of about 0.01% to about 5% and a suitable gelling agent in a range of about 0.001% to about 15% by weight of the composition.

Another feature of the present invention is the provision in the breakable nonflowing gel bait composition, of the combination of water in a range of about 40% to about 99% by weight of the composition, borax in a range of about 1.0% to about 5.0% by weight of the composition, glycerin in a range of about 2.0% to about 13% by weight of the composition, a sugar in an amount of about 15% to about 25% by weight of the composition, potassium sorbate (a preservative) in a range of about 0.01% to about 1%, and TICAGEL® (TIC Gums, 4609 Richlynn Drive, Belcamp, Md. 21017) in a range of about 0.1% to about 5.0% by weight of the composition.

An advantage of the present invention is that insects can land or crawl on the breakable nonflowing gel bait composition, remove some of the breakable nonflowing gel bait, and fly or crawl away back to their colonies without getting stuck in the breakable nonflowing gel bait composition, without dying, and without sending warning signals to other insects to avoid the breakable gel bait composition. The breakable nonflowing gel bait composition holds up the insect and does not allow the insect to get stuck in the composition.

Another advantage of the present invention is that, since insects can land on and take off, or crawl on and off, the breakable nonflowing gel bait composition, the entire surface area of the breakable nonflowing gel bait is available as a successful feeding area. In other words, the successful feeding area is not limited to just the edges of the breakable nonflowing gel bait composition.

Another advantage of the present invention is that the breakable nonflowing gel bait composition is not a liquid and thus not spillable.

Another advantage of the present invention is that the breakable nonflowing gel bait composition includes a high moisture content, but is not a liquid.

Another advantage of the present invention is that since the breakable nonflowing gel bait composition is not spillable or runny, the container in which it is deployed may be relatively simple in design, and still permit ready feeding by the target pest, without the bait contents spilling.

Another advantage of the present invention is that the bait container can be tossed or thrown into a difficult-to-access, or an inaccessible area, such as an attic or pipe chase, where pests may harbor, without the contents spilling out.

Another advantage of the present invention is that the breakable nonflowing gel bait composition remains in a single container throughout its lifetime as a product. For example, substantially immediately after being manufactured, the breakable nonflowing gel bait composition is poured into a container, then the container is sealed, then the container is shipped, then the container is opened in a predetermined manner such that the target pests may enter and feed, then the container is set out in its end use environment, and then the container having the breakable nonflowing gel bait composition is thrown away. Human contact with the breakable nonflowing gel bait composition is therefore minimized.

Another advantage of the present invention is that the breakable nonflowing gel bait composition retains its integrity as a breakable nonflowing gel even when set out in the hot sun.

Another advantage of the present invention is that a great variety of components can be placed into the framework of the breakable nonflowing gel. For example, a toxicant need not be water soluble. The toxicant is thoroughly dispersed in a heated breakable gel mixture and is trapped in the breakable nonflowing gel framework before the water-insoluble toxicant can settle out.

Another advantage of the present invention is that the breakable nonflowing gel bait composition is inexpensive. The components of the breakable nonflowing gel bait composition are inexpensive and the process of making the breakable nonflowing gel bait composition is inexpensive.

Another advantage of the present invention is that the breakable nonflowing gel bait composition is simple to manufacture in a minimal amount of time.

Another advantage of the present invention is that the breakable nonflowing gel bait composition is safe for shipping and requires no refrigeration during shipping.

Another advantage of the present invention is that the breakable nonflowing gel bait composition is safe for storage and requires no refrigeration while on the shelf.

Another advantage of the present invention is that the breakable nonflowing gel bait composition is simple and easy to use in the end use environment.

Another advantage of the present invention is that the breakable nonflowing gel bait composition is simple and easy to dispose of.

Another advantage is that the breakability of the breakable nonflowing gel provides a feature that permits pests to bite off and carry bits away to a nest, while the nonflowability of the same breakable nonflowing gel provides a feature that minimizes the chances of human contact with the toxicant of the gel.

DESCRIPTION

Figure 1A:
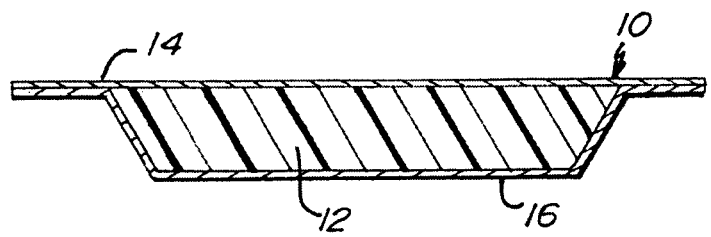
FIG. 1A is a section view of a container having the present breakable nonflowing gel bait composition therein, with the container having a peelable lid.

The present breakable nonflowing gel bait composition preferably includes a suitable gelling agent, a toxicant, a humectant, one or more attractants (foods and/or scents), and water. The breakable nonflowing gel bait composition is packaged in a ready-to-use bait placement container.

Physical Nature of the Breakable Nonflowing Gel Bait Composition

The gel bait composition is a breakable or cuttable gel. The gel form is such that when a force is applied to the gel, it may exhibit some initial elastic deformation, but ultimately the gel will fracture or break, rather than exhibit plastic flow. The most commonly recognizable example of a gel with this characteristic would be ordinary gelatin (when it is maintained at a sufficiently low temperature such that it doesn't melt).

The type of gel described in this invention is distinct from a smooth gel. A smooth gel may have a high moisture content, but its physical form is like that of a paste, i.e., it is smoothly smearable or spreadable. When sufficient force is applied to a smooth gel, it exhibits plastic flow. A smooth gel is not cut-able, breakable or friable into discreet pieces, nor does it exhibit a discreet rigid or semi-rigid integrity. Common examples of smooth gels would be dentifrice gels and hairstyling gels. It is possible for smooth gels to be "non-dripping" or non-flowing in certain circumstances, if they have sufficient body and viscosity, but smooth gels are not breakable or cut-able into discreet pieces.

The present breakable nonflowing gel bait composition can be breakable or cuttable into integral, one-piece, stand-alone pieces and still retain their integrity as breakable gels in such stand-alone pieces, and such stand-alone pieces can again be breakable or cuttable into integral, one-piece, stand-alone pieces that also retain their integrity as breakable gels. The stand-alone pieces can be in the form of disks or blocks or granules or any other shape or structure.

The present breakable nonflowing gel bait composition can be broken, cut or cleaved and does not reform without reheating to greater than its specific melting point. By reforming, what is meant is a rejoining of at least two separate broken, cut or cleaved gel pieces into a one-piece integral unit having an integrated network with the structural integrity of a breakable gel. The reforming or rejoining includes a heating step and a subsequent cooling step.

The present breakable nonflowing gel bait composition can be thermally reversible, where the temperature for such thermal reversibility is at or above about 100° F. If desired, the present breakable gel bait composition can be thermally irreversible.

The present breakable nonflowing gel bait composition can be a composition that maintains its integrity as a semi-rigid or rigid, breakable gel between about 32° F. and at least 100° F. In other words, the present breakable nonflowing gel bait composition maintains its integrity as a breakable gel even when deployed out in the sun where the breakable gel bait composition captures the heat of the sun or when the surface on which it is deployed captures the heat of the sun.

The present breakable nonflowing gel bait composition has minimal or no syneresis (weeping of water or solvent from the gelled network) at ambient or room temperature and further includes minimal or no syneresis up to its melting point of at least 100° F.

Minimal or no syneresis (weeping) of the present breakable nonflowing gel bait composition is important:

1) to prevent an insect or other pest from becoming stuck in the weeping or drown where there is excessive weeping;

2) to permit the insect to take a portion of the composition, including the toxicant, back to its colony;

3) to prevent the insect from incurring significant injury or death whereupon the insect may give off a signal warning other insects of the danger;

4) to permit an insect to feed over the entire surface of the breakable nonflowing gel bait composition, not merely at the edges; and 5) to permit an insect to take off and land on any portion of the surface of the breakable nonflowing gel bait composition.

The present breakable nonflowing gel bait composition can have a nonsticky, slippery surface with no syneresis.

The present breakable nonflowing gel bait composition can have a nonsticky, slippery surface with minimal syneresis.

The present breakable nonflowing gel bait composition has a pleasant non-sticky feel (to the touch of a finger) that is characteristic of a high water absorption rate. It should be noted that a relatively soft gel may have a low water absorption rate and a sticky feel.

It should be noted that a thixotropic gel is not a breakable gel. A thixotropic gel exhibits the property of becoming liquid when stirred or shaken.

Numerous natural gels and gums are capable of producing breakable nonflowing gels under certain conditions. Some of these include agars, pectins, cellulose gums, carrageenans, alginates and polyacrylamides. In practice, the companies that market gelling agents and gums take these natural products and chemically modify them, and in some cases blend them, to produce end-products that have specified desirable properties. One such product is TICAGEL® 121 (where TICAGEL® is a federally registered mark of TIC Gums, Inc. of Belcamp, Md.) which is a proprietary blend of carrageenan and cellulose gum, which has been used in a preferred embodiment of the present invention. A gel that readily exhibits plastic flow when force is applied is not a breakable nonflowing gel.

The breakable nonflowing gel preferably has a melting point of at least 100° F. The breakable nonflowing gel may have a melting point in a range of between about 100° F. and about 130° F.

The gelling agent or the gelling agents as a whole can be added to the breakable nonflowing gel bait composition in a range from preferably about 0.001% to about 25% by weight, more preferably about 0.001% to 20% by weight, and most preferably about 0.001% to about 15% by weight, of the weight of the breakable gel bait composition.

A preferred gelling agent for use in the present invention is TICAGEL® (TIC Gums, 4609 Richlynn Drive, Belcamp, Md. 21017). A gelling agent that produces the above described, desirable properties is preferred in the present invention.

The Toxicant

The toxicant for inclusion in the present breakable nonflowing gel bait composition can be a toxicant that is substantially water-soluble.

The toxicant for inclusion in the present breakable nonflowing gel bait composition can be a toxicant that is at least somewhat water-soluble.

The toxicant for inclusion in the present breakable nonflowing gel bait composition can be a toxicant that is present in a relatively small amount, and at such small amount the toxicant is water-soluble.

The toxicant for inclusion in the present breakable nonflowing gel bait composition can be a toxicant that is substantially not water-soluble. A toxicant that is substantially not water-soluble can be thoroughly dispersed in the present breakable nonflowing gel bait composition and then the mixture can be heated. When the composition is cooled, the toxicant that is substantially not water-soluble is relatively quickly trapped in the breakable nonflowing gel and thereby cannot settle out of the mixture.

The toxicant for inclusion in the present breakable nonflowing gel bait composition can be one or more of a delayed-action toxicant, contact toxicant, ingestion toxicant, fungi spore toxicant, or insect growth regulator.

The toxicant for inclusion in the present breakable nonflowing gel bait composition can be an insect toxicant or a rodent toxicant or a toxicant for some other pest.

The insect toxicant for inclusion in the present breakable nonflowing gel bait composition can be selected from one or more of the following toxicants: nithiazine, s-methyl-N-methylcarbamoyl, dimethoate, dimethyl (2,2,2-trichloro-1-hydroxyethyl)phosphonate, oxythioacelamidate, chlorpyrifos, propoxur, isofenphos, acephate, carbamates, organophosphates, chlorinated hydrocarbon insecticides, pyrethroids, sulfluramid, hydramethylnon, imidacloprid, boric acid, borax, other borate salts, avermectins, fenitrothion, fenthion, hexaflumuron, fenoxycarb, methoprene, hydroprene, diflubenzuron, pyriproxyfen, novaluron, or other insect growth regulators, Metarhizium, *Beauveria*, thiamethoxam, indoxacarb, dimethoate, phyloxine B, azinphosmethyl, diazinon, permethrin, pyrethrin, Malathion, Methomyl.

The rodent toxicant or rodenticide for inclusion in the present breakable nonflowing gel bait composition can be selected from one or more of the following toxicants: warfarin, diphacinone, sodium diphacinone, fumarin, fumasol, sulfaquinoline, zinc phosphide, strychnine, arsenic, bromethalin, chlorophacinone, coumachlor, coumatetralyl, discoumarin, pival, pivalyn, valone, sodium valone, 3-pyridylmethyl N-(4'-mercaptophenyl)carbamate and its derivatives, brodifacoum, difethialone, flocoumafen, bromadiolone, calciferol, ergocalciferol, cholecalciferol, difenacoum, or phenindione or combinations thereof.

The toxicant or the toxicants as a whole can be added to the breakable nonflowing gel bait composition in a range from preferably about 0.0001% to about 35% by weight, more preferably about 0.0001% to 30% by weight, and most preferably about 0.0001% to about 25% by weight, of the weight of the breakable gel bait composition.

Where the toxicant is borax, borax can be added to the breakable nonflowing gel bait composition in a range from preferably about 0.5% to about 10.0% by weight.

The Humectant

A humectant promotes the retention of moisture. A humectant is a hygroscopic substance. A hygroscopic substance is a substance that absorbs or attracts moisture from the air. Breakable nonflowing gels, including the breakable nonflowing gel bait composition of the present invention, may be porous and thereby expose a great amount of surface area of the breakable nonflowing gel to the atmosphere. Even if not porous, a breakable nonflowing gel may tend to lose moisture when exposed to the atmosphere.

While the inclusion of a humectant component in the breakable nonflowing gel bait composition is not required, the inclusion of a humectant component may be desirable when certain gelling agents are used or for certain end uses, such as in hot and dry environments. The inclusion of a humectant may also be important for the particular kind of animal, pest, insect or rodent because water can be an attractant for an animal, pest, insect or rodent. For example, mice are common pests in seed warehouses and, in such environments especially, the mice seek water and hence will seek a bait having moisture even where the bait includes no food; the water itself is an attractant.

The humectant herein can be a molecule with several hydrophilic groups such as hydroxyl groups, amine groups and carboxyl groups that have the affinity to form hydrogen bonds with molecules of water.

Humectants for inclusion in the breakable nonflowing gel bait composition can include polyols, glyceryl triacetate, lactic acid, urea, lithium chloride, alpha hydroxy acids, monosaccharides, polysaccharides, fructose, glucose, PCA, potassium lactate and PCA, sodium lactate and PCA, acetyl arginine, algae extract, aloe barbadensis leaf extract, 2,3-butanediol, chitosan lauroyl glycinate, diglycereth-7 malate, diglycerin, diglycol guanidine succinate, erythritol, fructose, glucose, honey, hydrolyzed wheat protein/polyethylene glycol-20 acetate copolymer, hydroxypropyltrimonium hyaluronate, hyaluronic acid, inositol, lactitol, maltose, mannitol, mannose, methoxy polyethylene glycol, myristamidobutyl guanidine acetate, polyglyceryl sorbitol, potassium PCA, propylene glycol, sodium PCA, sucrose, and natural extracts such as guillaia. Polyols include glycerin (glycerine or glycerol), diglycerin, and polyalkylene glycols. Polyols further include alkylene polyols and their derivatives. Polyols further include polyethylene glycol and derivatives thereof. Polyols further include butylene glycol, propylene glycol, pentylene glycol, dipropylene glycol, hexylene glycol, polypropylene glycol, sorbitol, xylitol, maltitol, other sugar alcohols, hydroxypropyl sorbitol, 1,2-butylene glycol, 1,2,6-hexanetriol, isoprene glycol, 2-methyl-1,3-propanediol, ethoxylated glycerol, propoxylated glycerol, PEG-4, and mixtures thereof. Polyols further include polymeric polyols such as polydextrose.

The humectant or the humectants as a whole can be added to the breakable nonflowing gel bait composition in a range from 0.0% (no humectant) to about 35% by weight, more preferably about 0.1% to 30% by weight, and most preferably about 0.1% to about 25% by weight, of the weight of the breakable nonflowing gel bait composition.

Where the humectant is glycerin, the glycerin can be added to the breakable nonflowing gel bait composition in a range from preferably about 1.0% to about 15% by weight, more preferably about 2.0% to 13% by weight, most preferably about 4.0% to about 11% by weight, and yet more preferably about 5.0% to about 10% by weight, of the weight of the breakable nonflowing gel bait composition.

The Attractant (Food)

The attractant can be a carbohydrate, protein, fat, cellulose, water, or nutrient or some combination thereof.

Carbohydrates include sugars, maltodextrins or starches or some combination thereof. The sugar can be a sugar selected from sucrose, fructose, D-fructose, glucose, maltose, trehalose, dextrose, lactose, honey, cane syrup, molasses, black sugar, brown sugar, soft brown sugar, a fruit juice, fruit, some other mono-, di- or tri-saccharide or mixtures thereof. Carbohydrates further include grains, vegetable seeds, peanut butter, syrups, cornmeal, corn, sweet corn, corn gluten, cereals, oatmeal, or pulverized cereal or mixtures thereof. Carbohydrates further include crop product powders such as potato starch, sweet potato starch, corn starch, wheat flour, rice powder, corn powder or mixtures thereof. Carbohydrates further include alcohols, beer, or wine.

Proteins include meat, poultry, poultry products, eggs, liver powder, egg powder, powdered yolk, fish meal, blood, blood products, meat by-products, powdered milk, soy, soy protein, vegetable protein, or some combination thereof.

Fats include oils, edible oils, animal oils, vegetable oils, edible fats, lard, bacon grease, soybean oil, rapeseed oil, sesame oil, rice bran oil, wheat germ oil, other seed oils, or some combination thereof.

Attractants further include substances that are not food such as pheromones and substances that include food odors but are not foods. A pheromone, such as n-heptyl butyrate or Periplanone B, is any chemical substance released by an animal that serves to influence the physiology or behavior of other members of the same species.

Substances that include food odors include foods and substances that are not food.

One substance that is not food that is an attractant is water or moisture. For example, mice in a seed warehouse will have ample food, but limited water.

Nutrients include amino acids. Amino acids include alanine, asparagine, aspartic acid, glutamic acid, glutamine, glycine, histidine, phenylalanine, proline, serine, threonine, or valine or some combination thereof.

The attractant or the attractants as a whole, where the attractant is not water, can be added to the breakable nonflowing gel bait composition in a range from 0.0% (no attractant or food) to about 49% by weight, more preferably about 0.1% to 49% by weight, and most preferably about 1.0% to about 49% by weight, of the weight of the breakable nonflowing gel bait composition.

Where the attractant is a sugar, the sugar can be added to the breakable nonflowing gel bait composition in a range from preferably about 10% to about 30% by weight, more preferably about 15% to 25% by weight, most preferably about 18% to about 22% by weight, and yet more preferably about 20% by weight, of the weight of the breakable nonflowing gel bait composition.

The Water Component

The water (or moisture) component of the present breakable nonflowing gel bait composition may be selected from tap water, distilled water, purified water, water purified by reverse osmosis, mineral water, filtered water, bottled water, spring water, fluorinated water, sea water, salt water, well water, municipality water, rain water, or some combination thereof.

The water can be added to the breakable nonflowing gel bait composition in a range from preferably about 30% to about 99% by weight, more preferably about 35% to about 99% by weight, and most preferably about 40% to about 99% by weight, of the weight of the breakable nonflowing gel bait composition.

Other Components

Other components that may be added to the breakable nonflowing gel bait composition include preservatives, antimicrobial agents, human aversion agents, or coloring agents. An example of a preservative is potassium sorbate. An example of a human aversion agent is a bittering agent such as, for example, denatonium benzoate.

Such other components are added to the breakable nonflowing gel bait composition in a range from 0.0% (no other component) to about 5.0% by weight, more preferably about 0.001% to 2.0% by weight, and most preferably about 0.001% to about 1.0% by weight, of the weight of the breakable nonflowing gel bait composition.

Method of Making

The method of making the present breakable nonflowing gel bait composition includes the steps of:

1) mixing all components except the gelling agent with each other, wherein this step of mixing can include the step of mixing all such components thoroughly with each other, wherein this step of mixing can include the step of heating the components, wherein this step of mixing can include the step of mixing at room temperature, 2) adding the gelling agent to the mixture and thoroughly mixing the gelling agent with the other components, 3) instead of steps 1 and 2, optionally mixing all components including the gelling agent with each other and thoroughly mixing all components with each other, 4) optionally heating the mixture, wherein the step of heating the mixture can start prior to or during the step of mixing all components with each other, wherein the step of heating can include the step of preheating one or more of the components prior to such component being added to the mixture, wherein the step of heating the mixture can include the step of heating the mixture to a temperature in a range from about 160° F. to about 200° F., more preferably from about 170° F. to about 190° F., and most preferably from about 175° F. to about 185° F., wherein the step of heating the mixture can include the step of further mixing, wherein the step of heating the mixture can include the step of keeping the mixture at a temperature in one of such ranges for a period of time of between about one minute and about two hours, more preferably about five minutes to two hours, and most preferably about ten minutes to one hour, wherein the step of heating can include the step of keeping the mixture at a temperature in one of such ranges or at another temperature until the components are even more thoroughly dispersed, wherein the step of heating can include the step of keeping the mixture at a temperature in one of such ranges or at another temperature until the gelling agent has attained a structure that, when cooled, produces a non-flowing, breakable gel, wherein the step of heating can include the step of keeping the mixture at a temperature in one of such ranges until the gel hydrates, and then 5) immediately pouring the heated mixture, if heated, into a plurality of individual receptacles or individual containers or permitting the heated mixture to at least partially cool whereupon the at least partially cooled and still flowing mixture is poured into a plurality of individual receptacles or containers. After being poured into the individual receptacle or containers, the mixture is allowed to attain ambient or room temperature to obtain the breakable nonflowing gel structure, thereby forming the breakable nonflowing gel bait composition.

The method of making can be carried out in a pot on a hot plate. The pot can include a mechanical mixer therein.

In an alternate method of making, the water and food (or attractant) components are mixed at room temperature, then the gelling agent is mixed in with the water and food, then a cross-linking agent (to cross-link the gelling agent) and toxicant component are mixed at room temperature apart from the water, food and gelling agent mixture. Then the cross-linking and toxicant mixture is mixed with the water, food and gelling agent mixture. Then the water, food, gelling agent, cross-linking agent and toxicant mixture is poured into an individual container. Then the water, food, gelling agent, cross-linking agent and toxicant mixture is permitted to stand for not less than 30 minutes in its individual container, in which the product remains for its entire life, including shipping, storage, deployment in the end-use environment, and disposal.

Shipping, Storing and Deployment of the Breakable Nonflowing Gel Bait Composition As indicated, the end result of the method of making is a breakable nonflowing gel bait composition in an individual receptacle or individual container. It is these containers having the breakable nonflowing gel bait composition therein, then, that are shipped, stored, sold and ultimately deployed in their end use environments such that the breakable nonflowing gel bait composition is neither squeezed, nor poured, nor scooped out of, nor otherwise removed from the individual receptacle or individual container in order to be deployed by the user. These containers may have peelable or otherwise removable lids or means of opening to allow the target pest to enter and feed. These containers may also be "place packs" or plastic bags through which an insect, rodent or other target pest can chew.

It should be noted that, if the breakable nonflowing gel bait composition is placed in a syringe and then the piston of the syringe is pushed into the cylinder of the syringe, then the breakable nonflowing gel bait composition may be pushed out of the needle portion of the syringe in a non-flowing manner (in a skidding manner) in which the breakable nonflowing gel bait composition will break down into small pieces during the relatively high pressure push by the piston. These small pieces may temporarily block the needle portion such that even greater pressure by the piston is required to force the small pieces through the nozzle or to force even further break down of such small pieces into smaller pieces that can skid through the nozzle of the syringe.

In other words, the breakable nonflowing gel bait composition has a first physical shape attained at manufacture (upon reaching ambient temperature or room temperature after being poured into the individual container). The breakable nonflowing gel bait composition has a second physical shape during shipping, during storage, and when deployed in an end use environment. And, since the breakable nonflowing gel bait composition is a non-flowing, breakable gel, the first physical shape and the second physical shape are substantially the same.

In still other words, the present invention contemplates one and only one container for the breakable nonflowing gel bait composition throughout its lifetime as a product such that the dedicated container is the container employed at manufacture and receives the breakable nonflowing gel bait composition when the breakable nonflowing gel bait composition is in a heated and flowing form, such that the same dedicated container is the container in which the gel bait composition cools to a breakable nonflowing gel form, and such that the same dedicated container is the container employed in an end use environment and is the container confronted by the pest that is being targeted. Throughout its lifetime as a product, the breakable nonflowing gel bait composition remains in the same container and is not transferred to another container in an end use environment. Even at the end of its lifetime, the product remains in the container for disposal. Such minimizes handling of the breakable gel bait composition by humans and thereby minimizes health concerns.

Several Types of Containers for the Breakable Nonflowing Gel Bait Composition

FIG. 1A is a section view of a container 10 having the present breakable nonflowing gel bait composition 12 therein, with the container 10 having a peelable lid 14 on a receptacle 16. The lid 14 is sealed at the factory and is removed at the end use setting.

Figure 1B:
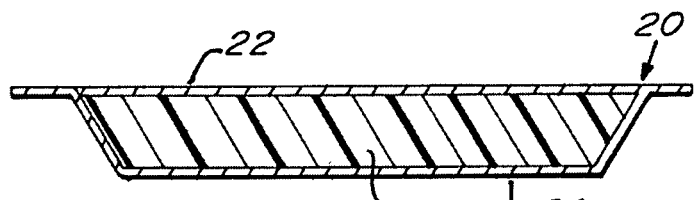
FIG. 1B is a section view of an alternate embodiment of a container having the present breakable nonflowing gel bait composition therein, wherein the lid is made integral, such as by welding, with the main body of the container, and wherein the container is formed of a chewable material.

FIG. 1B is a section view of an alternate embodiment of a container 20 having the present breakable nonflowing gel bait composition 12 therein, wherein a lid 22 is made integral, such as by welding, with the main body or receptacle 24 of the container 20, and wherein the container 20 is formed of a chewable material. The chewable material is preferably a plastic material that is chewable by an insect, rodent or other target pest. The plastic material, like most plastic material, is not perfectly airtight, and odors can permeate through the plastic material. The chewable material can be a wax.

Containers 10, 20 are breakable and self-supporting containers. Containers 10, 20 can be used for flying insects and have a pancake shape to provide a relatively great surface area for the flying insect to land and take off.

Figure 1C:
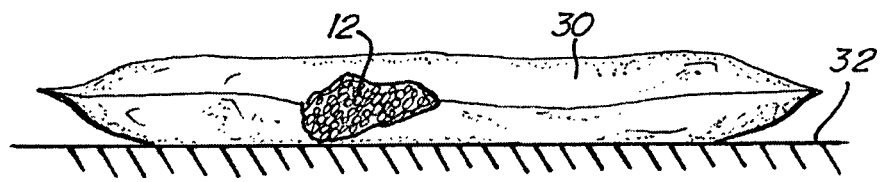
FIG. 1C is a partially cut away side view of a chewable plastic bag having the breakable nonflowing gel bait composition therein in a granular form.

FIG. 1C is a partially cut away side view of a chewable plastic bag 30 having the breakable nonflowing gel bait composition 12 therein in a granular form. Reference number 32 indicates a surface, such as a floor, upon which the chewable plastic bag 30 is placed for access by a pest.

Figure 1D:
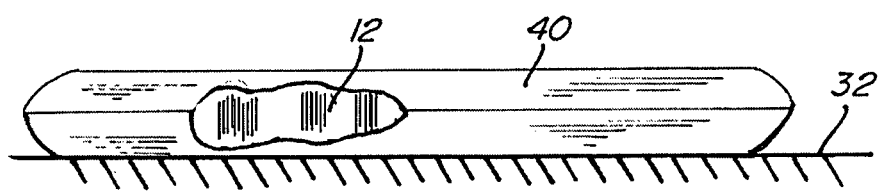
FIG. 1D is a partially cut away side view of a chewable plastic bag having the breakable nonflowing gel bait composition therein in a block form.

FIG. 1D is a partially cut away side view of a chewable plastic bag 40 having the breakable nonflowing gel bait composition 12 therein in a block form. Reference number 32 indicates a surface, such as a floor, upon which the chewable plastic bag 30 is placed for access by a pest.

Plastic bags 30 and 40 are flexible and have no defined opening. Plastic bags 30, 40 are sealed at the factory such as by being welded shut. Pests smell the breakable nonflowing gel bait composition through the bags 30, 40 and chew through the bag to get to the breakable nonflowing gel bait composition.

Example 1: Breakable Nonflowing Gel Bait Composition for Insects 714 grams of water, 30 grams of borax (an insect toxicant), 50 grams of glycerin (a humectant), and 200 grams of table sugar (sucrose), and 1.0 gram of potassium sorbate (a preservative) can be placed in a pot on a hot plate and the resulting mixture can be heated to about 185° F. and stirred until the components are thoroughly dispersed with each other. Then 5.0 grams of TICAGEL® 121 (TIC Gums, 4609 Richlynn Drive, Belcamp, Md. 21017) (a gelling agent having at least one of a kappa or iota carrageenan fraction and a cellulose fraction where TICAGEL® is a federally registered mark of TIC Gums, Inc. of 4609 Richlynn Drive, Belcamp, Md. 21017) can be added to the mixture while the mixture is being stirred and while maintaining the temperature at about 185° F. for about 15 minutes until the components are thoroughly dispersed in the mixture and until the gel hydrates. Then, substantially immediately, the mixture can be poured into 100 pancake shaped plastic containers having an interior volume of about 10 ml each. Then the mixture is permitted to cool to room temperature, during which the breakable nonflowing gel forms. Then a peelable lid is secured to the top of each of the pancake shaped containers, making each of the containers ready to be shipped.

Example 2: Breakable Nonflowing Gel Bait Composition for Insects 965 grams of water and 30 grams of borax (an insect toxicant) can be placed in a pot on a hot plate and the resulting mixture can be heated to about 185° F. and stirred until the components are thoroughly dispersed with each other. Then 5.0 grams of TICAGEL® 121 (a gelling agent having at least one of a kappa or iota carrageenan fraction and a cellulose fraction where TICAGEL® is a federally registered mark of TIC Gums, Inc. of Belcamp, Md.) can be added to the mixture while the mixture is being stirred and while maintaining the temperature at about 185° F. for about 15 minutes until the components are thoroughly dispersed in the mixture and until the gel hydrates. Then, substantially immediately, the mixture can be poured into 100 pancake shaped plastic containers having an interior volume of about 10 ml each. Then the mixture is permitted to cool to room temperature, during which the breakable nonflowing gel forms. Then a peelable lid is secured to the top of each of the pancake shaped containers, making each of the containers ready to be shipped.

Example 3: Breakable Nonflowing Gel Bait Composition for Insects

Example 1 is repeated, except that 664 grams of water and 100 grams of glycerin (a humectant) are used.

Example 4: Breakable Nonflowing Gel Bait Composition for Rodents

Example 1 is repeated, except that 0.05 grams of brodifacoum (a rodent toxicant) is used, instead of borax, along with an additional 29.95 grams of water.

Example 5: Breakable Nonflowing Gel Bait Composition for Roaches

This example provides a roach bait formula where no heating is required. At room temperature combine 400 grams of water and 570.5 grams of corn syrup until the corn syrup is fully blended with the water. While stirring, add 5.5 grams of TICAGEL® Algin (an alginate based gelling agent from TIC Gums, that produces a heat-irreversible gel when combined with Calcium ion, where TICAGEL® is a federally registered mark of TIC Gums, Inc. of Belcamp, Md.) and stir until the gelling agent is fully dissolved. Dry blend 2.5 g of Calcium Sulfate (a cross-linking agent) and 21.5 g of powdered Imidacloprid. Add the dry mixture to the gel solution and mix for 5 more minutes. Then the gel solution, having the dry mixture, may be poured into the desired container in which the gel will remain for its entire product life. After the step of pouring, the gel is allowed to form for not less than 30 minutes at room temperature, whereupon a breakable nonflowing gel is formed.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

I claim:

1. A breakable nonflowing gel bait composition comprising:
   a) water in a range of 55% to about 99% by weight of the composition;
   b) a pesticidal toxicant effective for rodents or insects in a range of about 0.0001% to about 25% by weight of the composition;
   c) a gelling agent in a range of about 0.001% to about 15% by weight of the composition; and
   d) wherein the composition is a breakable nonflowing gel between 32° F. and 100° F.;
   e) wherein the breakable nonflowing gel bait composition is breakable into integral, one-piece, stand-alone pieces and still retains integrity as a breakable nonflowing gel in said stand-alone pieces;
   f) wherein the breakable nonflowing gel bait composition is cuttable into two separate pieces and does not reform without reheating to greater than the melting point of the breakable nonflowing gel bait composition; and
   g) wherein the breakable nonflowing gel will fracture or break instead of exhibit plastic flow when a given force is applied thereto;
   h) such that pests can remove and consume or carry bits of said breakable nonflowing gel bait composition away to a nest.

2. The breakable nonflowing gel bait composition of claim 1, wherein the breakable nonflowing gel bait composition includes substantially no syneresis between about room temperature and at least about 100° F.

3. The breakable nonflowing gel bait composition of claim 1, wherein the breakable nonflowing gel bait composition has a non-sticky surface to the touch.

4. The breakable nonflowing gel bait composition of claim 1, and further comprising a humectant in a range of about 0.1% to about 25% by weight of the composition.

5. The breakable nonflowing gel bait composition of claim 1, and further comprising one or more attractants other than water in a combined range from about 1% to about 49% by weight of the composition.

6. The breakable nonflowing gel bait composition of claim 1, and further comprising a container for the breakable nonflowing gel bait composition.

7. The breakable nonflowing gel bait composition of claim 6, wherein the container may be opened in a predetermined manner to allow entrance and feeding by the target pest.

8. The breakable nonflowing gel bait composition of claim 6, wherein the container is a pest-chewable container having no defined opening.

9. A breakable nonflowing gel bait composition comprising:
   a) water in a range of 55% to about 99% by weight of the composition;
   b) a pesticidal toxicant effective for rodents or insects in a range of about 0.0001% to about 25% by weight of the composition;
   c) a humectant in a range of about 0.1% to about 25% by weight of the composition;
   d) an attractant in a range from about 1% to about 49% by weight of the composition;
   e) a gelling agent in a range of about 0.001% to about 15% by weight of the composition; and
   f) wherein the breakable nonflowing gel bait composition is a breakable nonflowing gel between 32° F. and 100° F.;
   g) wherein the breakable nonflowing gel bait composition is breakable into integral, one-piece, stand-alone pieces and still retains integrity as a breakable nonflowing gel in said stand-alone pieces;
   h) wherein the breakable nonflowing gel bait composition is cuttable into two separate pieces and does not reform without reheating to greater than the melting point of the breakable nonflowing gel bait composition; and
   i) wherein the breakable nonflowing gel will fracture or break instead of exhibit plastic flow when a given force is applied thereto;
   j) such that pests can remove and consume or carry bits of said breakable nonflowing gel bait composition away to a nest.

10. A breakable nonflowing gel bait composition comprising:
   a) water in a range of 55% to about 99% by weight of the composition;
   b) borax in a range of about 1.0% to about 5.0% by weight of the composition;
   c) glycerin in a range of about 2.0% to about 13% by weight of the composition;
   d) a sugar in an amount of about 15% to about 25% by weight of the composition;
   e) a gelling agent in a range of about 0.1% to about 1.0% by weight of the composition, wherein the gelling agent includes a carrageenan; and
   f) wherein the breakable nonflowing gel bait composition is a breakable nonflowing gel between 32° F. and 100° F.;
   g) wherein the breakable nonflowing gel bait composition is breakable into integral, one-piece, stand-alone pieces and still retains integrity as a breakable nonflowing gel in said stand-alone pieces;
   h) wherein the breakable nonflowing gel bait composition is cuttable into two separate pieces and does not reform without reheating to greater than the melting point of the breakable nonflowing gel bait composition; and i) wherein the breakable nonflowing gel will fracture or break instead of exhibit plastic flow when a given force is applied thereto;

j) such that pests can remove and consume or carry bits of said breakable nonflowing gel bait composition away to a nest.

11. A breakable nonflowing gel bait composition according to claim 10, wherein borax is in a range of about 2.0% to about 4.0% by weight of the composition, glycerin is in a range from about 4.0% to about 11% by weight of the composition, and a sugar is in a range from about 18% to about 22% by weight of the composition.

12. The breakable nonflowing gel bait composition according to claim 1, wherein the breakable nonflowing gel is not a paste.

13. The breakable nonflowing gel bait composition according to claim 1, wherein the breakable nonflowing gel is not a thixotropic gel.

14. The breakable nonflowing gel bait composition according to claim 1, wherein said gelling agent is a gelling agent selected from the group consisting of agars, pectins, cellulose gums, alginates, polyacrylamides, and a blend of carrageenan and cellulose gum.

15. A pesticidal bait comprising a breakable nonflowing gel between 32° F. and 100° F., wherein the breakable nonflowing gel is breakable into integral, one-piece, stand-alone pieces and still retains integrity as a breakable nonflowing gel in said stand-alone pieces, wherein the breakable nonflowing gel is cuttable into two separate pieces and does not reform without reheating to greater than the melting point of the breakable nonflowing gel, and wherein the breakable nonflowing gel will fracture or break instead of exhibit plastic flow when a given force is applied thereto, such that pests can remove and consume or carry bits of said breakable nonflowing gel away to a nest, and wherein the pesticidal bait further comprises a pesticidal toxicant in an effective concentration for rodents or insects.

16. The pesticidal bait of claim 15, wherein the pesticidal bait comprises a gelling agent in a concentration sufficient to yield the breakable nonflowing gel with a melting point in a range of 100° F. to about 130° F.

17. The pesticidal bait of claim 15, wherein the pesticidal bait comprises water in a range of about 30% to about 99% by weight.

18. The pesticidal bait of claim 15, wherein the breakable nonflowing gel includes substantially no syneresis between about room temperature and at least about 100° F.

19. The pesticidal bait of claim 15, wherein the breakable nonflowing gel has a non-sticky surface to the touch.

20. The pesticidal bait of claim 15, wherein the breakable nonflowing gel is a rigid gel and includes water.

21. The pesticidal bait of claim 15, wherein the breakable nonflowing gel includes water, and is capable of trapping a non-water soluble component within the gel framework.

* * * * *